United States Patent
Matsunaga et al.

(10) Patent No.: US 8,304,575 B2
(45) Date of Patent: Nov. 6, 2012

(54) PROCESS FOR PRODUCTION OF ETHER CARBOXYLATES

(75) Inventors: Akira Matsunaga, Wakayama (JP); Kaoru Ohmae, Wakayama (JP)

(73) Assignee: Kao Corporation, Tokyo (JP)

( * ) Notice: Subject to any disclaimer, the term of this patent is extended or adjusted under 35 U.S.C. 154(b) by 288 days.

(21) Appl. No.: 12/597,019

(22) PCT Filed: Apr. 3, 2008

(86) PCT No.: PCT/JP2008/056705
§ 371 (c)(1),
(2), (4) Date: Oct. 22, 2009

(87) PCT Pub. No.: WO2008/139790
PCT Pub. Date: Nov. 20, 2008

(65) Prior Publication Data
US 2010/0081716 A1    Apr. 1, 2010

(30) Foreign Application Priority Data
May 7, 2007    (JP) .................................. 2007-122572

(51) Int. Cl.
*C07C 59/00*    (2006.01)
(52) U.S. Cl. ........ 562/479; 562/400; 562/421; 514/557; 514/559; 514/560
(58) Field of Classification Search .................. None
See application file for complete search history.

(56) References Cited

U.S. PATENT DOCUMENTS

| 4,214,101 A | | 7/1980 | Miya et al. |
| 4,737,314 A | * | 4/1988 | Yokoyama et al. ........... 510/421 |

FOREIGN PATENT DOCUMENTS

| JP | 53 141218 | | 12/1978 |
| JP | 56 112931 | | 9/1981 |
| JP | 61 183241 | | 8/1986 |
| JP | 08-245499 | * | 9/1996 |
| JP | 8 283196 | | 10/1996 |
| JP | 2000 154163 | | 6/2000 |
| JP | 2003 277309 | | 10/2003 |
| JP | 2005 126432 | | 5/2005 |

OTHER PUBLICATIONS

JP 2003-277309, Suenaga, E. et al., Method for treating alkylene oxide adducts, 2003, English translation, 44 pages.*

* cited by examiner

*Primary Examiner* — Yate K Cutliff
(74) *Attorney, Agent, or Firm* — Oblon, Spivak, McClelland, Maier & Neustadt, L.L.P.

(57) ABSTRACT

The present invention relates to a process for producing an ether carboxylate which includes the steps of (1) reacting an aliphatic monohydric alcohol with an alkylene oxide in the presence of an alkali catalyst; (2) neutralizing a reaction solution obtained in the step (1) with an acid such as hydroxycarboxylic acids to obtain an ether alcohol; and (3-1) reacting the obtained ether alcohol with a monohalogenofatty acid or a salt thereof and an alkali metal hydroxide, or (3-2) subjecting the obtained ether alcohol to catalytic oxidation reaction in the presence of a catalyst. The obtained ether carboxylate has a less odor and a high quality and is therefore suitably used in the applications such as cosmetics and toiletries.

16 Claims, No Drawings

PROCESS FOR PRODUCTION OF ETHER CARBOXYLATES

CROSS REFERENCES TO RELATED APPLICATIONS

This application is a 371 of International Patent Application No. PCT/JP08/56705, filed on Apr. 3, 2008, and claims priority to Japanese Patent Application No. 2007-122572, filed on May 7, 2007.

FIELD OF THE INVENTION

The present invention relates to a process for producing a high quality ether carboxylate, and to a cosmetic composition and cosmetics and toiletries containing the ether carboxylate obtained by the process.

BACKGROUND OF THE INVENTION

Ether carboxylates, which have a high stability in hard water, a good detergency, an excellent environmental suitability such as good biodegradability and low fish toxicity, and a low skin irritation, are surfactants useful for use in skin care products such as shampoos, body cleansers and creams, dish washing detergents, bathroom and bathtub detergents, and house detergents.

Such an ether carboxylate is generally produced from an ether alcohol obtained by reacting an alcohol with an alkylene oxide in the presence of an alkali catalyst, followed by neutralization with acetic acid. More specifically, the ether alcohol is reacted with a monohalogenoacetic acid or its salt in the presence of an alkali metal hydroxide according to Williamson ether synthesis.

However, the ether carboxylate produced by the above method has an off-odor and is not satisfactorily used for products directly applied to human bodies such as shampoos and facial cleansers.

Patent Document 1 discloses a process for producing an ether carboxylate in which an aliphatic monohydric alcohol is reacted with an alkylene oxide in the presence of a quaternary ammonium salt to obtain an ether alcohol, and then the thus obtained ether alcohol is reacted with a monohalogenoacetic acid (or its salt) and an alkali metal hydroxide.

Patent Document 2 discloses a process for producing an ether carboxylate in which an aliphatic monohydric alcohol or its alkylene oxide adduct (ether alcohol) is reacted with a monohalogenated lower carboxylic acid salt and an alkali metal hydroxide in the form of beads while removing water under reduced pressure, if required, in the presence of a solvent.

Patent Document 3 discloses a process for producing an alkali salt of a carboxylic acid in which a terminal aliphatic monohydric alcohol of a polyoxyethylene chain-containing ether-type nonionic surfactant is oxidized with oxygen in the presence of a palladium catalyst.

However, Patent Documents 1 to 3 do not disclose nor suggest a method for improving an odor of the product.

Patent Document 4 discloses an ether alcohol which is stabilized by incorporation of lactic acid (or its salt) into an ether alcohol obtained by reaction of an aliphatic primary alcohol with ethylene oxide and which shows a less change in carbonyl value, acid value, pH, sulfuric acid wash color and odor. However, Patent Document 4 does not disclose nor suggest improvement of the odor of an ether carboxylate obtained using the ether alcohol as a raw material.

Patent Document 1: JP 08-283196A
Patent Document 2: JP 2000-154163A
Patent Document 3: JP 53-141218A
Patent Document 4: JP 61-183241A

SUMMARY OF THE INVENTION

The present invention provides the following aspects [1] to [3]:

[1] A process for producing an ether carboxylate, which includes the following step (1), step (2) and step (3-1) or step (3-2):

Step (1): reacting a $C_6$ to $C_{36}$ aliphatic monohydric alcohol with a $C_2$ to $C_4$ alkylene oxide in the presence of an alkali catalyst;

Step (2): neutralizing a reaction solution obtained in the step (1) with at least one acid selected from the group consisting of $C_2$ to $C_{10}$ hydroxycarboxylic acids, $C_2$ to $C_{10}$ dicarboxylic acids and $C_2$ to $C_{10}$ tricarboxylic acids to obtain an ether alcohol; and Step (3-1): reacting the ether alcohol obtained in the step (2) with a $C_2$ to $C_4$ monohalogenofatty acid or a salt thereof, and an alkali metal hydroxide; or Step (3-2): subjecting the ether alcohol obtained in the step (2) to catalytic oxidation reaction with oxygen or an oxygen-containing gas in the presence of a catalyst.

[2] A cosmetic composition including the ether carboxylate obtained by the process as defined in the above aspect [1].

[3] Cosmetics and toiletries including the ether carboxylate obtained by the process as defined in the above aspect [1].

DETAILED DESCRIPTION OF THE INVENTION

The present invention relates to a process for producing a high quality ether carboxylate having a less odor which is suitably used for cosmetics and toiletries, etc., and also relates to a cosmetic composition and cosmetics and toiletries including the ether carboxylate obtained by the process.

The present inventors have found that the above problem can be solved by reacting an aliphatic monohydric alcohol with an alkylene oxide in the presence of an alkali, neutralizing the resulting reaction solution with a specific carboxylic acid to obtain an ether alcohol, and then reacting the thus obtained ether alcohol with a monohalogenated lower fatty acid or a salt thereof. It has also been found that the above problem can be solved by subjecting the above ether alcohol to catalytic oxidation reaction in the presence of a catalyst.

That is, the present invention relates to the following aspects [1] to [3]:

[1] A process for producing an ether carboxylate, which includes the following step (1), step (2) and step (3-1) or step (3-2):

Step (1): reacting a $C_6$ to $C_{36}$ aliphatic monohydric alcohol with a $C_2$ to $C_4$ alkylene oxide in the presence of an alkali catalyst;

Step (2): neutralizing a reaction solution obtained in the step (1) with at least one acid selected from the group consisting of $C_2$ to $C_{10}$ hydroxycarboxylic acids, $C_2$ to $C_{10}$ dicarboxylic acids and $C_2$ to $C_{10}$ tricarboxylic acids to obtain an ether alcohol; and Step (3-1): reacting the ether alcohol obtained in the step (2) with a $C_2$ to $C_4$ monohalogenofatty acid or a salt thereof and an alkali metal hydroxide; or Step (3-2): subjecting the ether alcohol obtained in the step (2) to catalytic oxidation reaction with oxygen or an oxygen-containing gas in the presence of a catalyst.

[2] A cosmetic composition including the ether carboxylate obtained by the process as defined in the above aspect [1].

[3] Cosmetics and toiletries including the ether carboxylate obtained by the process as defined in the above aspect [1].

(Process for Production of Ether Carboxylate)

The process for producing an ether carboxylate according to the present invention includes the following steps (1), step (2) and step (3-1) or step (3-2):

Step (1): reacting a $C_6$ to $C_{36}$ aliphatic monohydric alcohol with a $C_2$ to $C_4$ alkylene oxide in the presence of an alkali catalyst;

Step (2): neutralizing a reaction solution obtained in the step (1) with at least one acid selected from the group consisting of $C_2$ to $C_{10}$ hydroxycarboxylic acids, $C_2$ to $C_{10}$ dicarboxylic acids and $C_2$ to $C_{10}$ tricarboxylic acids to obtain an ether alcohol; and Step (3-1): reacting the ether alcohol obtained in the step (2) with a $C_2$ to $C_4$ monohalogenofatty acid or a salt thereof and an alkali metal hydroxide; or Step (3-2): subjecting the ether alcohol obtained in the step (2) to catalytic oxidation reaction with oxygen or an oxygen-containing gas in the presence of a catalyst.

[Step (1)]

In the step (1) of the production process of the present invention, a $C_6$ to $C_{36}$ aliphatic monohydric alcohol is reacted with a $C_2$ to $C_4$ alkylene oxide in the presence of an alkali catalyst.

The $C_6$ to $C_{36}$ aliphatic monohydric alcohol is a compound represented by the following general formula (I):

$$R^1\text{—OH} \qquad (I).$$

In the general formula (I), $R^1$ is a saturated or unsaturated and linear, branched or cyclic aliphatic hydrocarbon group having 6 to 36 carbon atoms, preferably 8 to 30 carbon atoms and more preferably 8 to 22 carbon atoms.

Examples of the linear or branched alkyl group as $R^1$ include various octyl groups, various decyl groups, various dodecyl groups, various tetradecyl groups, various hexadecyl groups, various octadecyl groups, various eicosyl groups and various docosyl groups. Examples of the linear or branched alkenyl group as $R^1$ include various octenyl groups, various decenyl groups, various dodecenyl groups, various tetradecenyl groups, various hexadecenyl groups, various octadecenyl groups, various eicosenyl groups and various docosenyl groups. Examples of the cyclic aliphatic hydrocarbon group include a cyclooctyl group, a cyclodecyl group, a cyclododecyl group, a cyclooctenyl group, a cyclodecenyl group, a cyclododecenyl group, a 2-(cyclohexyl)ethyl group, a 3-(cyclohexyl)propyl group, a 2-(cyclohexenyl)ethyl group and a 3-(cyclohexenyl)propyl group.

As the $C_2$ to $C_4$ alkylene oxide, there may be mentioned, for example, ethylene oxide, propylene oxide and butylene oxide. Among these alkylene oxides, preferred are $C_2$ to $C_3$ alkylene oxides, and more preferred are ethylene oxide and a mixture of ethylene oxide and propylene oxide (propane-1,2-diyl oxide). From the viewpoint of good foamability and use feeling, the average molar number of the alkylene oxides added in the ether alcohol is from 0.1 to 100, more preferably from 0.1 to 50 and still more preferably from 0.1 to 20.

Examples of the alkali catalyst used in the step (1) include alkali metal hydroxides and alkali metal alkoxides. From the viewpoint of economy, among these catalysts, preferred are potassium hydroxide and sodium hydroxide, and more preferred is potassium hydroxide. The alkali catalyst is preferably used in an amount of from 0.001 to 0.1 mol, more preferably from 0.001 to 0.05 mol and still more preferably from 0.001 to 0.02 mol per 1 mol of the aliphatic monohydric alcohol.

The temperature at which the aliphatic monohydric alcohol is reacted with the alkylene oxide is preferably from 50 to 180° C. and more preferably from 60 to 160° C. The reaction is preferably carried out under pressure. The reaction pressure is more preferably from 0.1 to 0.5 MPa.

[Step (2)]

In the step (2), the reaction solution obtained in the preceding step (1) is neutralized with at least one acid selected from the group consisting of $C_2$ to $C_{10}$ hydroxycarboxylic acids, $C_2$ to $C_{10}$ dicarboxylic acids and $C_2$ to $C_{10}$ tricarboxylic acids to obtain an ether alcohol.

As the $C_2$ to $C_{10}$ hydroxycarboxylic, dicarboxylic and tricarboxylic acids used in the step (2), there may be preferably used, for example, at least one acid selected from the group consisting of lactic acid, glyceric acid, malonic acid, glycolic acid, citric acid and malic acid. Among them, preferred are one of the acids which have a solubility in water of 50% by volume or more, and a mixture of any two or more of these acids, and more preferred are lactic acid and glyceric acid.

The acid is preferably used in an amount of from 0.5 to 3.0 mol and more preferably from 0.8 to 1.5 mol, in terms of the amount of carboxylic acid groups used for the neutralization, per 1 mol of the alkali catalyst.

With the above neutralization, there may be obtained an ether alcohol in which the alkylene oxide is added in an amount of preferably from 0.1 to 100 mol, more preferably from 0.1 to 50 mol and still more preferably from 0.1 to 20 mol, on average, per 1 mol of the aliphatic monohydric alcohol.

[Step (3-1)]

In the step (3-1), the ether alcohol obtained in the above step (2) is reacted with a $C_2$ to $C_4$ monohalogenofatty acid or a salt thereof, and an alkali metal hydroxide.

As the $C_2$ to $C_4$ monohalogenofatty acid or a salt thereof used in the step (3-1), there may be mentioned a compound represented by the following general formula (II):

$$XR^2\text{—COO}^-.1/n M^{n+} \qquad (II).$$

In the general formula (II), $R^2$ is a $C_1$ to $C_3$ alkanediyl group such as a methylene group, an ethylene group, a trimethylene group and a propane-1,2-diyl group; X is a halogen atom, preferably a chlorine atom or a bromine atom; M is a hydrogen atom, an alkali metal, an alkali earth metal, ammonium, a lower alkanolamine (such as monoethanolamine, diethanolamine and triethanolamine) or the like; and n is a valency of M.

The $C_2$ to $C_4$ monohalogenofatty acid or a salt thereof represented by the general formula (II) is preferably a monohalogenoacetic acid or a monohalogenoacetic acid salt. Examples of the monohalogenoacetic acid include monochloroacetic acid and monobromoacetic acid. Examples of the monohalogenoacetic acid salt include sodium monochloroacetate, sodium monobromoacetate, potassium monochloroacetate acid and potassium monobromoacetate.

The monohalogenoacetic acid or salt thereof may be used in the form of either a powder or an aqueous solution. In the case where the monohalogenoacetic acid or salt thereof is used as an aqueous solution, the concentration thereof is from about 50 to about 90% by mass and preferably from 75 to 85% by mass.

As the alkali metal hydroxide used in step (3-1), sodium hydroxide and potassium hydroxide are preferred from the viewpoint of economy. The alkali metal hydroxide may be used in the form of a solid such as a powder, beads or pellets, or may be used in the form of an aqueous solution. From the viewpoint of product quality, the alkali metal hydroxide is preferably used in the form of a solid such as beads and pellets.

When used as a solid, the alkali metal hydroxide is preferably in the form of beads or pellets, more preferably in the form of beads and still more preferably in the form of beads having such a particle size distribution that 80% by mass or more of the beads have a particle diameter of from about 0.2 to about 2 mm (80% by mass or more of the beads can pass through a 8 mesh sieve, and 20% by mass or less of the beads can pass through a 80 mesh sieve). In the case where the alkali metal hydroxide is used as an aqueous solution, the concentration thereof is from about 30 to about 60% by mass and preferably from 45 to 55% by mass.

The carboxymethylation of the ether alcohol in the step (3-1) may be carried out, for example, by any of the following steps (a) to (c).

<Step (a)>

In the step (a), an alkali metal salt of a monohalogenoacetic acid in the form of a powder and an alkali metal hydroxide in the form of a powder, beads or other solids are added to and reacted with the ether alcohol.

The molar ratio of the powdery alkali metal salt of monohalogenoacetic acid to the ether alcohol is preferably from 0.8 to 2.0 and more preferably from 1.0 to 1.5, whereas the molar ratio of the alkali metal hydroxide in the form of a powder, beads or other solids to the alkali metal salt of monohalogenoacetic acid is preferably from 1.0 to 1.5.

The reaction temperature is preferably from 50 to 90° C. and more preferably from 68 to 80° C., and the reaction time is preferably from 1 to 24 h and more preferably from 3 to 6 h. The reaction may be carried out while intermittently or continuously adding the respective reactants. If necessary, the reaction may be carried out while removing water produced in situ during the reaction under reduced pressure or under a nitrogen flow. If necessary, after completion of the addition of the reactants, the reaction mixture may be aged for several hours under the same conditions or other conditions to complete the reaction.

<Step (b)>

In the step (b), while maintaining a mixture of the ether alcohol and a monohalogenoacetic acid or a salt thereof at a temperature of preferably from 50 to 100° C. and more preferably from 70 to 80° C., an aqueous solution of an alkali metal hydroxide is added dropwise to and reacted with the mixture under reduced pressure of preferably from 0.67 to 26.6 kPa and more preferably from 1.33 to 5.32 kPa.

The monohalogenoacetic acid or a salt thereof is preferably used in an amount of from 0.8 to 2.0 mol and more preferably from 1 to 1.5 mol per 1 mol of the ether alcohol, whereas the alkali metal hydroxide is used in an amount of from 2.0 to 3.0 mol per 1 mol of the monohalogenoacetic acid, and is used in an amount of from 1 to 1.5 mol per 1 mol of the monohalogenoacetic acid salt.

The dropping time of the alkali metal hydroxide aqueous solution is preferably from 0.5 to 10 h and more preferably from 1 to 3 h. Although the reaction is almost completed upon the termination of the dropping, the reaction mixture may be aged, if necessary, for several hours under the same conditions or other conditions to complete the reaction.

<Step (c)>

In the step (c), while maintaining the ether alcohol at a temperature of preferably from 50 to 100° C. and more preferably from 70 to 80° C., an aqueous solution of a monohalogenoacetic acid or a salt thereof and an aqueous solution of an alkali metal hydroxide are simultaneously added dropwise to and reacted with the ether alcohol under reduced pressure of preferably from 0.67 to 26.6 kPa and more preferably from 1.33 to 5.32 kPa.

The monohalogenoacetic acid or a salt thereof is preferably used in an amount of from 0.8 to 2.0 mol and more preferably from 1 to 1.5 mol per 1 mol of the ether alcohol, whereas the alkali metal hydroxide is used in an amount of from 2.0 to 3.0 mol per 1 mol of the monohalogenoacetic acid and is used in an amount of from 1 to 1.5 mol per 1 mol of the monohalogenoacetic acid salt.

The dropping time of the monohalogenoacetic acid aqueous solution and the alkali metal hydroxide aqueous solution is preferably from 0.5 to 10 h and more preferably from 1 to 3 h, whereas the dropping time of the monohalogenoacetic acid salt aqueous solution and the alkali metal hydroxide aqueous solution is preferably from 0.5 to 5 h and more preferably from 1 to 3 h. When a monohalogenoacetic acid is used, the alkali metal hydroxide aqueous solution is always added in a slightly larger amount than the monohalogenoacetic acid aqueous solution so that the pH is maintained in the range of from about 8 to about 13 during the reaction. Although the reaction is almost completed upon the termination of the dropping, the reaction mixture may be aged, if necessary, for several hours under the same conditions or other conditions to complete the reaction.

The crude reaction mixture obtained in any of the above steps (a) to (c) may be subjected to a post treatment by a variety of methods. Examples of the method for the post treatment include (1) a method in which the crude reaction mixture is added and diluted with water such that the solid content after dryness is about 30% by mass, and the resulting mixture is adjusted to pH of from about 6 to about 8 by adding hydrochloric acid, sulfuric acid or the like thereto, and (2) a method in which the crude reaction mixture is rendered acidic by adding hydrochloric acid thereto, and the resulting mixture is allowed to stand to separate an oil layer which is then washed. In the method (2), the washed oil layer may be used as such in its intended applications. Alternatively, the oil layer may be neutralized with sodium hydroxide, potassium hydroxide, magnesium hydroxide, calcium hydroxide or the like and converted into a salt to use the resulting product in its intended applications.

[Step (3-2)]

In the step (3-2), the ether alcohol obtained in the above step (2) is subjected to catalytic oxidation reaction with oxygen or an oxygen-containing gas in the presence of a catalyst.

The catalyst used in the step (3-2) is not specifically limited and may be, for example, at least one catalyst selected from the group consisting of platinum, palladium, selenium, tellurium, antimony, tin, bismuth and lead. Among these catalysts, a platinum catalyst and/or a palladium catalyst are preferred. The catalysts may be used alone or in combination of any two or more thereof.

The catalyst is generally preferably used in the form of a supported catalyst. Any known carrier may be used without specific limitation. Examples of the carrier include activated carbon, asbestos, silica, activated clay and alumina. Among these carriers, activated carbon is preferred. It is preferred that the activated carbon be previously refined by an ordinary method for improving a catalytic activity thereof. The amount of the catalyst component supported on the carrier is generally from 0.05 to 10% by mass and preferably from 1 to 8% by mass. A particularly preferable catalyst is a catalyst containing platinum and/or palladium supported in an amount of from 1 to 10% by mass and preferably from 2 to 8% by mass, on activated carbon.

When silica, an alkali earth metal element, zinc or a compound of a transition metal is added to the catalyst, the durability and activity of the catalyst and the color tone of the ether carboxylate as a product obtained by the oxidation may be improved.

The above catalyst may be produced by a known method. For example, a catalyst containing, as catalytic components, palladium and the other metal (such as tellurium) supported on activated carbon as a carrier may be produced as follows. First, activated carbon is dispersed in ion-exchanged water. A hydrochloric acid aqueous solution containing palladium chloride and a chloride of the other metal (such as tellurium chloride), as raw materials for the catalytic components, is prepared and mixed with the previously prepared activated carbon dispersion by an ordinary method so that the catalytic components are adsorbed on the activated carbon. The mixture thus produced after the adsorption treatment may be subjected to a reduction treatment with formalin, hydrazine, sodium borohydride, hydrogen, etc., under heating, followed by separating the catalyst from the mixture by filtration and, if necessary, further drying the thus separated catalyst, to obtain the desired catalyst.

When the ether alcohol obtained in the step (2) is oxidized using the catalyst, it is preferred that the oxidation reaction be carried out in an aqueous solvent maintained at a pH of 7.5 or higher and preferably from 8 to 10, from the viewpoints of the reaction rate and the color tone of the ether carboxylate produced. Since the pH of the reaction mixture decreases as the oxidation reaction proceeds, it is preferable to carry out the oxidation reaction while adding an alkali thereto and neutralizing. The alkali is preferably sodium hydroxide or potassium hydroxide. Although the amount of the alkali added may be a theoretical equimolar amount relative to the amount of the ether alcohol to be oxidized, the alkali is preferably used in an excess molar amount that is larger by several % than the amount of the ether alcohol. The alkali is generally used in the form of an aqueous solution, and may be charged in its whole amount at one time at an early stage of the reaction or may be continuously or intermittently added while maintaining the reaction mixture at a suitable pH.

The reaction temperature is generally from 30 to 100° C., preferably from 40 to 90° C. and more preferably from 50 to 80° C. The reaction pressure is generally from 0.03 to 0.50 MPa, preferably from 0.05 to 0.4 MPa and more preferably from 0.07 to 0.30 MPa, and the reaction time is preferably from 1 to 24 h, more preferably from 1 to 15 h and still more preferably from 1 to 10 h.

The catalytic oxidation reaction of the ether alcohol may also be carried out, for example, by introducing oxygen, an oxygen-containing gas obtained by diluting oxygen with nitrogen or the like, or air into the reaction mixture while bubbling at an elevated temperature in the above-described range in the presence of the above-described catalyst under stirring.

According to the above-described methods, an ether carboxylate represented by the following general formula (III) can be produced in the step (3-1), whereas an ether carboxylate represented by the following general formula (IV) can be produced in the step (3-2):

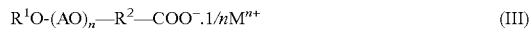
(III)

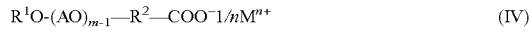
(IV)

wherein A is a $C_2$ to $C_4$ alkanediyl group; m represents an average molar number of addition of AO groups and lies in the range of from 0.1 to 100; and $R^1$, $R^2$, M and n are the same as defined previously.

In the general formulae (III) and (IV), the alkanediyl group represented by A is preferably at least one group selected from the group consisting of an ethylene group, a trimethylene group and a propane-1,2-diyl group, and is more preferably an ethylene group or a mixed group of ethylene and propane-1,2-diyl.

The number m is preferably from 0.1 to 50 and more preferably from 0.1 to 20.

$R^2$ is preferably a methylene group, and $M^{n+}$ is preferably a sodium ion from the viewpoints of foamability, detergency and economy.

(Cosmetic Compositions, and Cosmetics and Toiletries)

The ether carboxylate produced by the process of the present invention may be extensively used in various applications as a detergent, a softening agent, a wetting agent, a dying assistant, etc., and is particularly useful for use in products directly applied to human bodies such as shampoos and facial cleansers, because of its less odor and high quality.

Upon producing a detergent composition containing the ether carboxylate produced by the process of the present invention, various surfactants commonly used for the production of detergent compositions may be incorporated in any optional proportion in addition to the ether carboxylate. Examples of the surfactant include anionic surfactants, nonionic surfactants, cationic surfactants and amphoteric surfactants.

These surfactants may be used alone or in the form of a mixture of any two or more thereof. It is, however, particularly preferable to use an anionic surfactant alone or to use combination of an anionic surfactant and a nonionic surfactant. The amount of the surfactant used varies depending upon type of the composition, and is preferably from 0.1 to 60% by mass and more preferably from 1 to 50% by mass on the basis of a total mass of the detergent composition.

The detergent composition may be produced by an ordinary method. The detergent composition may be used in any optionally selected form, for example, in the form of a liquid, a paste, a solid or a powder. Among these types of detergent compositions, preferred are a liquid and a paste.

The ether carboxylate produced by the process of the present invention has a less odor, an excellent foamability and an excellent detergency as well as a low toxicity and a low skin irritation and, therefore, is useful for use in products that are brought into direct contact with the skin for a long period of time such as shampoos and body shampoos, namely is useful as a cosmetic composition, cosmetics and toiletries, a detergent such as kitchen cleansers, etc.

The term "cosmetic composition" as used herein is intended to include skin cosmetic compositions and makeup cosmetic compositions. The term "cosmetics and toiletries" as used herein is intended to refer to products for use in making people's appearance clean or beautiful and to include, for example, toilet waters, lotions, body shampoos, milky lotions, skin milks, creams, facial cleansers, hair shampoos, bath agents, antiperspirants and soaps.

EXAMPLES

In the following Examples and Comparative Examples, "%" means "% by mass" unless otherwise specified.

Example 1

[Step (1)]

A 3 L autoclave made of SUS and used as a reaction vessel, was charged with 1,326.5 g (7.12 mol) of lauryl alcohol (KALCOL 2098 available from Kao Corp.) and 1.0 g (0.018 mol) of potassium hydroxide in the form of flakes (available from Nippon Soda Co., Ltd.), and then an interior of the reaction vessel was substituted with nitrogen. The contents of the reaction vessel were heated to 110° C. while stirring, and the pressure within the reaction vessel was reduced to 13 Pa with a vacuum pump to remove water therefrom for 1 h (amount of water removed was 0.7 g). After the inside temperature of the reaction vessel was raised to 155° C., 941 g (21.36 mol) of an ethylene oxide gas were gradually added thereto over 2 h. The resulting reaction mixture was then aged under heating for 1 h while stirring (final pressure: 0.4 MPa) and then cooled to 80° C. Thereafter, the pressure within the reaction vessel was reduced to 4 kPa to remove an unreacted ethylene oxide gas under the same condition for 30 min.

[Step (2)]

The pressure within the reaction vessel was returned to the atmospheric pressure by feeding a nitrogen gas thereto. Then, 1.8 g (0.018 mol) of a 90% lactic acid aqueous solution was added to neutralize the potassium hydroxide. The product obtained after the completion of the reaction was withdrawn from a drain at a lower portion of the reaction vessel to obtain 2,265 g of an ether alcohol (adduct having an average molar number of addition of ethylene oxides of 3; average molecular weight: 318.5).

[Step (3-1)]: Carboxymethylation Reaction

A 2 L reaction vessel was charged with 990.5 g (3.11 mol) of the ether alcohol (average molecular weight: 318.5) obtained in the above step (2). While stirring and mixing under a nitrogen flow, the contents of the reaction vessel were heated to 70 to 75° C. Then, 388.1 g (3.27 mol) in total of sodium monochloroacetate (SMCA; molecular weight: 116.5; purity: 98%) and 130.6 g (3.27 moles) in total of sodium hydroxide in the form of beads (85% or more of the beads passed through a 8 mesh sieve, and 15% or less of the beads passed through a 80 mesh sieve) were added in equally divided five parts to the reaction vessel in which the first part was added at the start of the reaction and the second to fifth parts were intermittently added at the intervals of 1 h. After completion of adding the whole amounts of the compounds, the reaction mixture was aged under heating for 1 h. Next, the reaction temperature was raised to 85° C. at which the reaction mixture was further aged under heating for 1 h to obtain an ether carboxylate. To the thus obtained product, 35% hydrochloric acid was added until the pH reached 2.8. Water was then added until the precipitated sodium chloride was completely dissolved. The resulting solution was stirred at 90° C. for 1 h and then allowed to stand at 90° C. for 1 h to separate an oil layer therefrom. The oil layer thus obtained was neutralized with a sodium hydroxide aqueous solution to obtain a 25% aqueous solution of a sodium salt of ether carboxylate.

Example 2

The same procedure as in Example 1 was repeated except that in the step (3-1) of Example 1, sodium hydroxide in the form of pellets (particle diameter: 5 to 8 mm) was used in place of the sodium hydroxide in the form of beads, thereby obtaining a 25% aqueous solution of a sodium salt of ether carboxylate.

Example 3

The same procedure as in Example 1 was repeated except that in the step (3-1) of Example 1, an ether alcohol obtained after storing the ether alcohol produced in the step (2) of Example 1 at 40° C. for 30 days was used, thereby obtaining a 25% aqueous solution of a sodium salt of ether carboxylate.

Comparative Example 1

[Production of Ether Alcohol]

In the same manner as that in the step (1) of Example 1, lauryl alcohol was reacted with ethylene oxide. Then, the same procedure as in the step (2) of Example 1 was repeated except that 1.1 g (0.018 mol) of acetic acid was used in place of lactic acid for the neutralization of potassium hydroxide, thereby obtaining 2,265 g of an ether alcohol (adduct having an average molar number of addition of ethylene oxides of 3; average molecular weight: 318.5).

[Carboxymethylation Reaction]

A 2 L reaction vessel was charged with 990.5 g (3.11 mol) of the above obtained ether alcohol (average molecular weight: 318.5). While stirring and mixing under a nitrogen flow, the contents of the reaction vessel were heated to 70 to 75° C. Then, 388.1 g (3.27 mol) in total of sodium monochloroacetate (SMCA; molecular weight: 116.5; purity: 98%) and 130.6 g (3.27 mol) in total of sodium hydroxide in the form of pellets (particle diameter: 5 to 8 mm) were added in equally divided five parts to the reaction vessel in which the first part was added at the start of the reaction and the second to fifth parts were intermittently added at the intervals of 1 h. After completion of adding the whole amounts of the compounds, the reaction mixture was aged under heating for 1 h. Next, the reaction temperature was raised to 85° C. at which the reaction mixture was further aged under heating for 1 h to obtain an ether carboxylate. To the thus obtained product, 35% hydrochloric acid was added until the pH reached 2.8. Water was then added until the precipitated sodium chloride was completely dissolved. The resulting solution was stirred at 90° C. for 1 h and then allowed to stand at 90° C. for 1 h to separate an oil layer therefrom. The oil layer thus obtained was neutralized with a sodium hydroxide aqueous solution to obtain a 25% aqueous solution of a sodium salt of ether carboxylate.

Comparative Example 2

The same procedure as in the step of Comparative Example 1 was repeated except for using an ether alcohol obtained after storing the ether alcohol produced in Comparative Example 1 at 40° C. for 30 days, thereby obtaining a 25% aqueous solution of a sodium salt of ether carboxylate.

Example 4

A 3 L reaction vessel was charged with 990.5 g (3.11 mol) of the ether alcohol (average molecular weight: 318.5) obtained in the same manner as in the step (2) of Example 1. While stirring and mixing, the contents of the reaction vessel were heated to 70 to 75° C., and then 952.2 g (3.27 mol) of a 40% sodium monochloroacetate aqueous solution and 272.5 g (3.27 mol) of a 48% sodium hydroxide aqueous solution were added dropwise into the reaction vessel over 5 h under reduced pressure of 4 kPa. The water contained in the 40% sodium monochloroacetate aqueous solution and the 48% sodium hydroxide aqueous solution and the water produced during the reaction were condensed in a cooling trap and withdrawn out of the system. After completion of adding the whole amounts of the compounds, the resulting reaction mixture was aged under heating for 1 h. Next, the reaction temperature was raised to 85° C. at which the reaction mixture was further aged under heating for 1 h to obtain an ether carboxylate. To the thus obtained product, 35% hydrochloric acid was added until the pH reached 2.8.

Water was then added until the precipitated sodium chloride was completely dissolved. The resulting solution was stirred at 90° C. for 1 h and then allowed to stand at 90° C. for 1 h to separate an oil layer therefrom. The oil layer thus obtained was neutralized with a sodium hydroxide aqueous solution to obtain a 25% aqueous solution of a sodium salt of ether carboxylate.

Comparative Example 3

The same procedure as in Example 4 was repeated except for using the ether alcohol obtain in the same manner as in Comparative Example 1, thereby obtaining a 25% aqueous solution of a sodium salt of ether carboxylate.

Example 5

A 2 L reaction vessel was charged with 159.3 g (0.50 mol) of the ether alcohol (average molecular weight: 318.5) obtained in the same manner as in the step (2) of Example 1, 41.7 g (0.50 mol) of a 48% sodium hydroxide aqueous solution and 800 g of water into which 8 g of a palladium catalyst supported on activated carbon (Pd was supported in an amount of 5% by mass) was suspended. The contents of the reaction vessel were heated to 70 to 75° C. while stirring and mixing, and reacted for 6 h while bubbling an oxygen gas under normal pressures therethrough to obtain an ether carboxylate. After the catalyst was separated by filtration, 35% hydrochloric acid was added to the obtained ether carboxylate until the pH reached 2.8. The resulting reaction mixture was stirred at 90° C. for 1 h and then allowed to stand at 90° C. for 1 h to separate an oil layer therefrom. The oil layer thus obtained was neutralized with a sodium hydroxide aqueous solution to obtain a 25% aqueous solution of a sodium salt of ether carboxylate.

Comparative Example 4

The same procedures as in Example 5 was repeated except for using the ether alcohol obtain in the same manner as in Comparative Example 1, thereby obtaining a 25% aqueous solution of a sodium salt of ether carboxylate.

Example 6

A 2 L reaction vessel was charged with 159.3 g (0.50 mol) of the ether alcohol (average molecular weight: 318.5) obtained in the same manner as in the step (2) of Example 1 and 800 g of water into which 8 g of a platinum catalyst supported on activated carbon (Pt was supported in an amount of 5% by mass) was suspended. The contents of the reaction vessel were heated to 70 to 75° C. while stirring and mixing, and reacted for 12 h while bubbling an oxygen gas under normal pressures therethrough to obtain an ether carboxylate. After the catalyst was separated by filtration, the obtained ether carboxylate was stirred at 90° C. for 1 h and then allowed to stand at 90° C. for 1 h to separate an oil layer therefrom. The oil layer thus obtained was neutralized with a sodium hydroxide aqueous solution to obtain a 25% aqueous solution of a sodium salt of ether carboxylate.

Comparative Example 5

The same procedures as in Example 6 was repeated except for using the ether alcohol obtain in the same manner as in Comparative Example 1, thereby obtaining a 25% aqueous solution of a sodium salt of ether carboxylate.

Experimental Example 1

The 25% aqueous solution of sodium salt of ether carboxylate obtained in each of Examples 1 to 6 and Comparative Examples 1 to 5 was placed in an amount of 25 g in a 50 mL screw vial. Sensory evaluation (evaluation of odor) was carried out at an opening top of each vial by four panelists (healthy persons). Specifically, the sensory evaluation was performed according to the following six ratings including Ranks 0 to 5, and the respective evaluation results were expressed as an average value of scores of the Ranks given by the four persons. The results are shown in Table 1.

Evaluation Ratings of Odor:
0: No odor
1: Slight, unrecognizable odor
2: Weak but recognizable odor
3: Clearly recognizable odor
4: Strong odor
5: Terrible odor

TABLE 1

|  | Odor evaluation | Kind of odor |
|---|---|---|
| Example 1 | 1 | No acid odor was recognized |
| Example 2 | 2 | Weak oil odor was recognized |
| Example 3 | 1 | No acid odor was recognized |
| Comparative Example 1 | 3 | Acid odor was recognized |
| Comparative Example 2 | 4 | Strong acid odor and oil odor were recognized |
| Example 4 | 1 | No acid odor was recognized |
| Comparative Example 3 | 3 | Acid odor was recognized |
| Example 5 | 1 | No acid odor was recognized |
| Comparative Example 4 | 3 | Acid odor was recognized |
| Example 6 | 1 | No acid odor was recognized |
| Comparative Example 5 | 3 | Acid odor was recognized |

In the following, there is shown a formulation example of a cosmetic composition using the 25% aqueous solution of sodium salt of ether carboxylate obtained in Example 1.

Formulation Example 1

Body Shampoo:

| | | |
|---|---|---|
| (a) | Sodium lauryl ether sulfate (effective component: 27%; molar number of addition of EO: 2) | 30% |
| (b) | Ether carboxylate obtained in Example 1 (25% sodium salt aqueous solution) | 10% |
| (c) | Lauroylamidopropyl dimethyl carboxybetaine | 3% |
| (d) | Lauryl dimethyl hydroxysulfobetaine | 2% |
| (e) | Coconut oil fatty acid | 2% |
| (f) | Dibutyl hydroxytoluene | 0.1% |
| (g) | Ethanol | 2% |
| (h) | Perfume | 0.5% |
| (i) | Water | balance |

According to the above formulation, the above components (a) to (f) were added to and dissolved in hot water (i). The obtained solution was cooled and then added with the above components (g) and (h) to obtain a transparent body shampoo. The skin was washed using the body shampoo. It was found that the shampoo had a low skin irritation, a good foamability and an excellent use feeling. Further, there occurred such a feeling that a good fragrance given by the shampoo was continuously emitted during the washing.

Industrial Applicability

The ether carboxylate produced by the process of the present invention has substantially no acid odor as observed in the conventional products and is particularly suitable as a surfactant for use in cosmetics and toiletries.

The invention claimed is:

1. A process for producing an ether carboxylate, comprising:
   (1) reacting a $C_6$ to $C_{36}$ aliphatic monohydric alcohol with a $C_2$ to $C_4$ alkylene oxide in the presence of an alkali catalyst, to obtain a reaction solution;
   (2) neutralizing said reaction solution with at least one acid selected from the group consisting of a $C_2$ to $C_{10}$ hydroxycarboxylic acid, a $C_2$ to $C_{10}$ dicarboxylic acid, and a $C_2$ to $C_{10}$ tricarboxylic acid, to obtain an ether alcohol; and
   (3-1) reacting said ether alcohol with a $C_2$ to $C_4$ monohalogenoacetic acid or a salt thereof and an alkali metal hydroxide, to obtain said ether carboxylate,
   wherein said reacting said ether alcohol with said $C_2$ to $C_4$ monohalogenoacetic acid or a salt thereof and said alkali metal hydroxide is conducted by simultaneously adding an aqueous solution of said $C_2$ to $C_4$ monohalogenoacetic acid or a salt thereof and an aqueous solution of said alkali metal hydroxide drop-wise to said ether alcohol, while maintaining said ether alcohol at a temperature of 50 to 100° C. and under a reduced pressure of 0.67 to 26.6 kPa.

2. The process for producing an ether carboxylate according to claim 1, wherein said reaction solution is neutralized with at least one acid selected from the group consisting of lactic acid, glyceric acid, malonic acid, glycolic acid, citric acid, and malic acid.

3. The process according to claim 1, wherein said reaction solution is neutralized with 0.5 to 3.0 equivalents of said acid in terms of the number of carboxylic acid groups in said acid per each mole of said alkali catalyst.

4. The process according to claim 1, wherein said reaction solution is neutralized with 0.8 to 1.5 equivalents of said acid in terms of the number of carboxylic acid groups in said acid per each mole of said alkali catalyst.

5. The process according to claim 1, wherein said reacting of said $C_6$ to $C_{36}$ aliphatic monohydric alcohol with said $C_2$ to $C_4$ alkylene oxide in the presence of said alkali catalyst is conducted with 0.001 to 0.1 moles of said alkali catalyst per 1 mole of said $C_6$ to $C_{36}$ aliphatic monohydric alcohol.

6. The process according to claim 1, wherein said reacting of said $C_6$ to $C_{36}$ aliphatic monohydric alcohol with said $C_2$ to $C_4$ alkylene oxide in the presence of said alkali catalyst is conducted with 0.001 to 0.05 moles of said alkali catalyst per 1 mole of said $C_6$ to $C_{36}$ aliphatic monohydric alcohol.

7. The process according to claim 1, wherein said reacting of said $C_6$ to $C_{36}$ aliphatic monohydric alcohol with said $C_2$ to $C_4$ alkylene oxide in the presence of said alkali catalyst is conducted with 0.001 to 0.02 moles of said alkali catalyst per 1 mole of said $C_6$ to $C_{36}$ aliphatic monohydric alcohol.

8. The process according to claim 1, wherein said reacting of said $C_6$ to $C_{36}$ aliphatic monohydric alcohol with said $C_2$ to $C_4$ alkylene oxide in the presence of said alkali catalyst is conducted at a temperature of 50 to 180° C. and a pressure of 0.1 to 0.5 MPa.

9. The process according to claim 1, wherein said reacting of said $C_6$ to $C_{36}$ aliphatic monohydric alcohol with said $C_2$ to $C_4$ alkylene oxide in the presence of said alkali catalyst is conducted at a temperature of 60 to 160° C. and a pressure of 0.1 to 0.5 MPa.

10. The process according to claim 1, wherein said ether alcohol is reacted with said 0.8 to 2.0 moles of said $C_2$ to $C_4$ monohalogenoacetic acid or a salt thereof per 1 mole of said ether alcohol.

11. The process according to claim 1, wherein said ether alcohol is reacted with said 1 to 1.5 moles of said $C_2$ to $C_4$ monohalogenoacetic acid or a salt thereof per 1 mole of said ether alcohol.

12. The process according to claim 1, wherein said ether alcohol is reacted with the 2.0 to 3.0 moles of said alkali metal hydroxide per 1 mole of said monohalogenoacetic acid.

13. The process according to claim 1, wherein said ether alcohol is reacted with the 1 to 1.5 moles of said alkali metal hydroxide per 1 mole of said monohalogenoacetic acid.

14. The process according to claim 1, wherein said aqueous solution of said $C_2$ to $C_4$ monohalogenoacetic acid or a salt thereof and said aqueous solution of said alkali metal hydroxide are added drop-wise to said ether alcohol over a time of 0.5 to 10 hours.

15. The process according to claim 1, wherein said aqueous solution of said $C_2$ to $C_4$ monohalogenoacetic acid or a salt thereof and said aqueous solution of said alkali metal hydroxide are added drop-wise to said ether alcohol over a time of 1 to 3 hours.

16. The process according to claim 1, wherein said reacting said ether alcohol with said $C_2$ to $C_4$ monohalogenoacetic acid or a salt thereof and said alkali metal hydroxide is conducted by simultaneously adding an aqueous solution of said $C_2$ to $C_4$ monohalogenoacetic acid or a salt thereof and an aqueous solution of said alkali metal hydroxide drop-wise to said ether alcohol, while maintaining said ether alcohol at a temperature of 70 to 80° C. and under a reduced pressure of 1.33 to 5.32 kPa.

\* \* \* \* \*